United States Patent [19]

Ramsland

[11] Patent Number: 4,632,762
[45] Date of Patent: Dec. 30, 1986

[54] CENTRIFUGAL CHROMATOGRAPHY

[76] Inventor: Arnold Ramsland, 121 S. Kingman Rd., South Orange, N.J. 07079

[21] Appl. No.: 738,297

[22] Filed: May 28, 1985

[51] Int. Cl.[4] .......................... B01D 15/08; C02F 1/28
[52] U.S. Cl. .................................. 210/657; 210/198.2; 210/198.3
[58] Field of Search ................... 210/657, 198.2, 198.3

[56] References Cited
U.S. PATENT DOCUMENTS
3,395,093 7/1968 Liberti .............................. 210/198.3

Primary Examiner—Frank Sever
Attorney, Agent, or Firm—Laughlin, Markensohn, Lagani & Pegg

[57] ABSTRACT

Separation of liquid mixtures is achieved through a chromatographic method by employing centrifugal force in combination with dielectrophoretic force. The dielectrophoretic force is generated by electrostatically charging a flat rotatable surface. The resulting non-uniform electrical field acts on the liquid that is applied to the surface.

8 Claims, 1 Drawing Figure

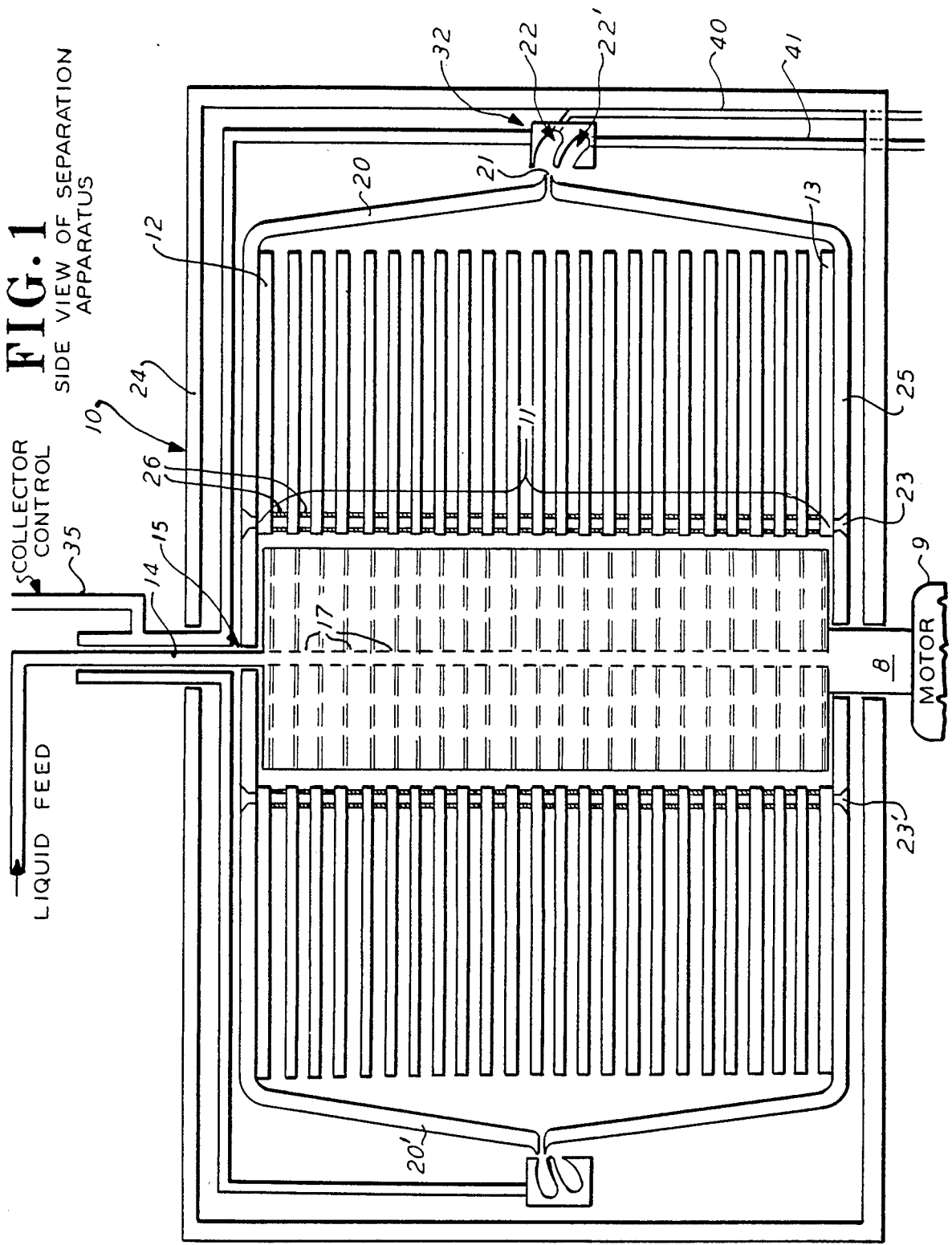

CENTRIFUGAL CHROMATOGRAPHY

This invention relates to apparatus and a method for separating liquids which are miscible at the temperature of separation.

BACKGROUND OF THE INVENTION

Chromatography has found wide spread use in the analytical separation of components in liquid or gas mixtures. The term chromatography is generally applied to all multiple partitioning of mixtures that lead to individual zones of migration for components of the mixture. Chromatography involves a mobile phase and a stationary phase. The molecules of the mixture migrate along the stationary phase at a rate proportional to their relative affinities for the mobile and stationary phases. The volume of mobile phase required for separation is usually orders of magnitude greater than the volume of solute molecules separated. Because of this a second separation is usually required to recover the desired molecules from the mobile phase. This drawback has generally limited the applicability of chromatography to small-scale separations.

It is known to use counter current chromatography as a method for separating liquids by utilizing the hydrodynamic behavior of the two immiscible solvents in a rotating coiled tube. It is further known to use a centrifugal type liquid chromatography whereby centrifugal force is used to push a mobile phase across a spinning disk coated with a stationary phase. It is also known to use electrostatic charge in the separation of solids.

OBJECTS OF THE INVENTION

It is an object of this invention to provide an apparatus which utilizes centrifugal force in the chromatographic separation of liquids without the use of a mobile phase. It is another object of this invention to provide a process whereby components of a mixture migrate at different rates across a smooth or lightly abraded surface which is electrostatically charged and thereby achieve separation. It is a further object of this invention to achieve separation in a cost effective and energy efficient manner. Other objects and the advantages of the invention will appear from the following detailed description.

SUMMARY OF THE INVENTION

In accordance with the invention, it has been found that a high degree of separation of a liquid mixture can be achieved by utilizing a chromatographic method without a mobile phase. This separation is obtained by making use of centrifugal force in combination with dielectrophoretic force. Dielectrophoretic force acting upon neutral liquids can be created by electrostatically charging a flat surface. This electrostatic charging introduces a non-uniform electrical field which acts as a force upon a liquid adhering to the surface. As an illustration, if the molecules of the liquid are neutral, two behaviors are observed in response to the dielectrophoretic force. The first behavior is paraelectric behavior which is observed in many organic molecules such as ethanol. If the surface is positively charged, the ethanol molecules will develop a dipole with the negative charge on the end nearest the positive surface. In a non-uniform field, the molecule is attracted more strongly toward the surface than away from it. In such an instance the molecule is drawn toward the higher strength field. This behavior can be observed by applying a drop of ethanol to an electrostatically charged surface. The drop migrates radially outward to maximize surface coverage.

The opposite behavior in response to dielectrophoretic force is apoelectric behavior. This type of behavior results when a molecule is a spinning, permanent dipole. An example of this is water. A spinning, permanent dipole will be oriented in all possible configurations with respect to the electric field. A time averaging of all configurations will show no preferential molecular polarity with respect to the field. The result is apoelectric behavior where the molecule moves away from the highest strength field. A drop of water "beads up" in order to minimize surface coverage.

The apparatus of the invention comprises a number of vertically stacked flat disks which are electrostatically charged. The whole disk can be charged or a number of areas or spots on both the top and bottom surfaces can be charged. The action of the electrostatically charged surface substitutes for the action of the stationary phase in the chromatographic procedure.

In operation the liquid mixture is sprayed on the surface of the rotating disk at the inner portion. This spraying can be considered the equivalent of injection or spotting in ordinary chromatography. The spinning creates a centrifugal force which causes the liquid mixture to migrate from the inner portion to the outer perimeter of the surface of the disk.

The disks can be made of either a conducting material or a non-conducting (dielectric) material. If a conducting material (such as a metal foil or conducting plastic film) is used, an auxiliary high voltage power supply is used to create an electrostatic charge on the surface. One can also use a non-conducting material such as a plastic film. This can be done by treating the dielectric to create a permanent electrostatic charge. The term electret is used to describe a dielectric which has been treated to give a permanent (or very long lasting) electrostatic charge. One can do this by subjecting a thin plastic to a high voltage corona discharwge. This and other techniques used in making electrets are described in the scientific literature, see for example A. D. Moore, *Electrostatics and Its Applications,* Wiley-Interscience, New York, 1972. Thin film mylar has been found to be particularly suitable because of its charge stability, strength, machining properties and chemical inertness. It is important that the disk surface be relatively smooth so that no physical barriers obstruct the migration of the liquid.

The apparatus heretofore described has been found to be especially applicable in the separation of organic molecules such as ethanol, methanol and acetic acid from water. The reasons for this special applicability is that water and these organic compounds show opposite behaviors toward dielectrophoretic force. As a general rule, the greater the difference between the behavior of molecules in the partitioning between two phases, the easier the separation will be. Another reason is that an electrostatic field reduces the hydrogen bonding between ethanol and water. Hydrogen bonding results because there is an electrical attraction between the dipolar molecules of ethanol and water. A strong electrostatic field induces a dipole in ethanol which competes with the neighboring water molecules for electrical attraction. It has been observed that there is a repulsion between drops of ethanol and water on a charged surface.

This invention has a further advantage in that it can also be used for the separation of ethanol, methanol and acetic acid from larger organic molecules as well as from each other. It is believed that the explanation for this capability is that the paraelectric behavior toward dielectrophoretic force diminishes as the molecules increase in size. It can be seen therefore that compounds can be separated based upon the extent of their paraelectric behavior.

In carrying out the process, a mixture of two or more components is sprayed onto the inner surface of a spinning disk stack. In the case of ethanol and water, ethanol migrates somewhat faster because the highest field strength is immediately in front of the zone of liquid migration. The separated (or partially separated) liquids are collected as they are thrown off the outer edge of the disks. The cycle is then repeated. It is recognized that the cycle time can be decreased by increasing the rotation speed after the elution of the first component. It is also recognized that a method of energy storage can be employed if the rotation speed is changed.

FIG. 1 shows the best mode of the invention.

Referring to FIG. 1 of the drawing, a disk stack 11 is rigidly supported by upper support disk 20 and a lower support disk 25. The liquid to be separated is fed into the center of the disk stack 11 through a tube 14 which passes through an opening 15 in the upper support disk 20. The tube 14 is perforated 17 adjacent to the disk stack 11 so that an even spray is achieved in the vertical direction. It has been found effective to increase the diameter of the feed tube adjacent to the disk stack so that air space and thus liquid evaporation is minimized. By spraying onto a spinning disk stack, an even spray is achieved radially. It is recognized that other equivalent means can be used to apply the mixture evenly to the inside surface of the disk stack. The spray will adhere to the inner surface of both centrifugal force and capillary action.

The lower support disk 25 is affixed to shaft 8 from a drive motor 9. The motor is preferably equipped with a variable drive to allow for changes in the speed of rotation. The support disks are bent at the outside perimeter 20 toward the vertical middle of the disk stack. This configuration concentrates the liquids which have exited from the disk stack by forcing them through a small gap 21 between the support disks prior to entering a collector 22. This concentration of liquid minimizes the surface area so that evaporation is minimized in the liquid transfer to the collector. A series of drive bolts 23 between the upper disk and lower support disk provides for rotation of the entire disk stack. The drive bolts are electrically connected to a high voltage power supply (not shown) when conducting disks are used. The drive bolts and the surrounding metal spacers 26 supply an electrostatic charge to the disks from one electrode of the power supply. The other electrode is connected to a ground. The drive bolts are located toward the inner diameter of the disk stack so that the spacers around the drive bolts in combination with centrifugal force can be used to maintain a desired gap between the disks. The gap can vary but distances from 0.005 to 0.015 inches are usually suitable. The disks are preferably very thin which increases capacity, reduces weight and permits electret formation. The thickness of the disks can vary but a thickness from 0.001 to 0.016 inches has been found to be generally suitable.

A non-rotating collector 32 of generally cylindrical design is used to collect the liquids after separation. This collector has two channels 22 and 22'. The collector moves in a vertical direction by a control 35 so that a desired liquid or liquid fraction passes into a desired channel. A microprocessor driven control (not shown) of the spraying and collector movement in each cycle is preferred.

As indicated the collector 32 has two channels 22 and 22'. Each channel is designed to gravity feed into exit tubes 40 and 41. The exit tubes then feed into separate collector vessels. The gap between the rotating support disks and the stationary collector is minimized to keep air turbulence at a low level.

The disk dimensions determine the capacity and efficiency of liquid separation. An increase in the inside diameter of the separating disks results in a corresponding increase in the injection spray volume and capacity. The difference between the inside and outside diameters affects the efficiency of the separation. If that distance is too small, insufficient liquid migration occurs and efficiency will be diminished. If the distance is too large, the liquid spreads too thinly over the disk surface. This both slows and degrades the separation. A distance between eight and twelve inches has generally been found to be suitable. The speed of revolution of the disks also affects the separation. That speed should be sufficient to cause migration but not so large that the centrifugal force overwhelms the dielectrophoretic force. Generally, it has been found that low speeds (100–300 RPM) are suitable.

The advantages of this invention may be more readily appreciated by reference to the following example.

EXAMPLE

EXPERIMENTAL CONDITIONS

Disk Preparation: A 0.005" mylar film (type A) was subject to a 10,000 volt corona discharge.

Disk Dimensions: 8" inner diameter, 15" outer diameter

Disk Gap: 0.005"

Spray Volume: 0.25 milliliters (ML) per disk.

Rotation Speed: 200 RPM

RESULTS

A 50/50 mixture of ethanol/water was sprayed onto the inner diameter of a disk stack. After 15 seconds the collector was switched from channel 1 to channel 2. The composition in channel 1 was found to be approximately 70/30 ethanol/water. The rotation speed was then increased to 500 RPM. The composition in channel 2 was found to be approximately 30/70 ethanol/water. The volumes collected in each channel were approximately equal.

While the invention has been described with reference to its preferred embodiments, it will be appreciated by those of ordinary skill in the art that various changes can be made without departing from the scope of the invention and such modifications are intended to be included within the scope of the claims.

What is claimed is:

1. A chromatographic process which comprises: separating the major component of a mixture of two or more liquids having different affinities for electrostatic charge while precluding the need for utilizing a mobile phase by applying at least partially an electrostatic charge to a flat, smooth, non-absorbent disk, rotating said disk in a horizontal plane, feeding a mixture of at least two such liquids on to the inner surface of said disk and collecting the respective liquids thrown from the outer edge of the rotating disk at different time intervals.

2. The process of claim 1 wherein the liquid mixtures are selected from the group consisting of ethanol and water, methanol and water, and acetic acid and water.

3. The process of claim 1 wherein the disk has a surface of mylar.

4. An apparatus comprising means for separating two or more components of a liquid mixture having different affinities for an electrostatically charged surface while precluding the need for utilizing a mobile phase component utilizing a flat, smooth, non porous disk, means for rotating said disk in a generally horizontal plane, means for applying said liquid mixture onto the inner surface of said disks and means for collecting the liquid as it leaves the outer edge of the disk at different times.

5. The apparatus of claim 4 wherein the disk has a surface of mylar.

6. The apparatus of claim 4 wherein a plurality of disks are utilized.

7. The apparatus of claim 6 wherein the gap between the disks is from about 0.005 to about 0.015 inches.

8. The apparatus of claim 6 wherein the means for collecting the liquid is only movable in the vertical direction.

* * * * *